United States Patent [19]
Tickner et al.

[11] Patent Number: 5,333,613
[45] Date of Patent: Aug. 2, 1994

[54] MICROPARTICLES AS ULTRASONIC CONTRAST MEDIA

[75] Inventors: Ernest G. Tickner, Coulterville; Robert E. Short, Los Gatos; David H. Rammler, Woodside, all of Calif.

[73] Assignee: Delineate, Menlo Park, Calif.

[21] Appl. No.: 35,466

[22] Filed: Mar. 23, 1993

[51] Int. Cl.$^5$ .............................................. A61B 8/00
[52] U.S. Cl. ........................... 128/662.02; 128/660.01
[58] Field of Search .................. 128/660.01, 662.02, 128/661.08

[56] References Cited

U.S. PATENT DOCUMENTS

| | | | |
|---|---|---|---|
| 4,265,251 | 5/1981 | Tickner | 128/662.02 |
| 4,276,885 | 7/1981 | Tickner et al. | 128/662.02 |
| 4,442,843 | 4/1984 | Rasor et al. | 128/662.02 |
| 4,466,442 | 8/1984 | Hilmann et al. | 128/662.02 |
| 4,718,433 | 1/1988 | Feinstein | 128/662.02 |
| 5,088,499 | 2/1992 | Unger | 128/662.02 |

OTHER PUBLICATIONS

Bommer et al., "Indicator–dilution curves obtained by photometric analysis of two–dimension echo-contrast studies", *American Journal of Cardiology*, 41:370 (1978) (Abstract).

Feigenbaum et al., "Identification of ultrasound echoes from the left ventricle by use of intracardiac injections of indocyanine green", *Circulation*, 41:615–621 (1970).

Gramiak et al., "Ultrasound cardiography: Contrast studies in anatomy and function", *Radiology*, 92:939–948 (1969).

Meltzer et al., "The source of ultrasound contrast effect", *J. Clin. Ultrasound*, 8:121–127 (1980).

*Primary Examiner*—William E. Kamm
*Assistant Examiner*—George Manuel
*Attorney, Agent, or Firm*—Bertram I. Rowland

[57] ABSTRACT

Ultrasonic contrast media are provided comprising small particles with entrapped gas, where the compositions can be selected for rapid dissolution with production of microbubbles or maintaining the gas in microtubules, microchambers or microcracks, providing for echogenicity. The particles are readily formed by precipitation from a liquid, either solution or melt, of a monomeric material, followed by drying and mechanically reducing the size of the particles.

6 Claims, No Drawings

MICROPARTICLES AS ULTRASONIC CONTRAST MEDIA

INTRODUCTION

Technical Field

The field of this invention is gaseous particulate contrast media.

Background

Ultrasonic waves are compression waves passing through a media with a frequency above the upper audible frequency range taken to be 20 kilohertz. Clinical ultrasound is generally in the low to medium megahertz frequency regime. Large gas volumes are too large to render useful ultrasonic utility because they are so echogenic that sound waves cannot pass through them to interact with underlying structure. However, very small gas volumes are extremely useful for this purpose to delineate structures using clinical ultrasound. Gas is a compressible substance and very small gas volumes, whether bubbles, gas tubules or channels, exhibit this property. Thus, gas microvolumes exposed to ultrasonic signals respond by going to compressional oscillation. Gas volumes experiencing compressional oscillation reradiate compression waves and therefore act as superior reflectors. A homogeneous distribution of microbubbles within a liquid can serve as a sensitive indicator of boundaries and interfaces because of this characteristic. Contrast agents are frequently used in medicine to differentiate subtle differences between two areas to effect a diagnosis. Although contrast agents have been used clinically in x-ray technology for many years, this has not been the case with ultrasound. While a number of attempts have been made to use gas bubbles and produce gas bubbles in a variety of ways for contrast agents, these various techniques fall short of optimum for a variety of reasons. There is, therefore, substantial interest in providing for novel means for providing ultrasound contrast for clinical diagnosis.

RELEVANT LITERATURE

Gramiak and Shah, *Echocardrograpy of the Aortia Root, Invest. Radiol.* (1969) 92, 939 and Feigenbaum, et al., *Circulation* (1970) 41, 616 reported seeing clouds of echos in cardiac chambers following injection of various agents. These investigators speculated that microbubbles were the source of this effect. Meltzer, et al., *J. Clin. Ultrasound* (1980) 8, 121 indicated that microbubbles could be used for ultrasonic contrast. Ticknet and Rasor, NIH *Annual Report* (1977) HR-62917-1A developed a microbubble contrast agent. Then, Bommer, et al., *Circulation* (1980) 62 (II), 94 demonstrated the efficacy of this contrast substance. An early technique employed to produce bubbles for clinical applications described by was to vigorously agitate a medium such as saline, D5W, cardiogreen dye, blood or x-ray dye, just prior to injection into the bloodstream.

U.S. Pat. No. 4,466,442 described a three-part system where a vial of gas, a liquid containing a surface tension reducing substance and a viscosity enhancer were combined.

U.S. Pat. No. 4,276,885 describes microbubbles with precise diameters formed with a coalescent resistant skin, preferably made of gelatin.

U.S. Pat. No. 4,265,251 employs a fused saccharide encapsulating pressurized microbubbles. Bubbles are released as the saccharide dissolves in the bloodstream.

U.S. Pat. No. 4,442,843 employs microparticles maintained in a dry state, which are then mixed with a carrier liquid in which the precursor is soluble. Air bubbles are trapped between the particles. The microbubbles are stabilized by the viscous liquid formed by the solvation of the particle material.

U.S. Pat. No. 4,718,433 produces encapsulated microbubbles within human albumin shells.

SUMMARY OF THE INVENTION

Individual microparticles are provided which are formed to capture gas in small volumes within the particles. These particles are selected to provide for a relatively low or relatively high medium solubility, where the velocity of the capillary front or wicking in a capillary channel in the particle is either relatively greater or relatively less than the velocity of dissolution of the particle. The particle may be coated with various water resistant coatings to reduce hydration. The particles may be administered orally, by an aerosol or intravascularly.

DESCRIPTION OF THE SPECIFIC EMBODIMENTS

Individual microparticles are provided for contrast media or ultrasonic detection of surfaces in chambers, particularly biological chambers. The particles are characterized by being small, encapsulating gas, wherein depending upon the nature of the composition of the matrix particle, either retain the gas to provide the echogenic effect or release the gas as microbubbles to provide the echogenic effect. The compositions are selected so as to have a relatively low or relatively high solubility in an aqueous medium, particularly a physiological fluid, e.g. blood, under physiological conditions. The particles are introduced in a moderately viscous aqueous medium, which allows for decreasing coalescence of released microbubbles. Depending upon the application, the particles will be stable in the environment into which they are introduced for at least about 1 min and may provide echogenic properties for three hours or substantially more if provided with a low permeability coating.

The ultrasonic contrast agents of the subject invention are characterized by being: physiologically acceptable (in the environment in which they are introduced) solid particles of at least about 0.5 $\mu$ with entrapped gas; echogenic (i.e., capable of reflecting sound waves); varying in size from small enough to pass through capillaries to large enough to have long residence times in the gastrointestinal tract and accepted by the gastrointestinal tract or specific portions thereof; substantially reproducible in properties and response as a contrast agent, and have long shelf-life when stored with reasonable precautions.

For the most part, the matrix particles will vary in size and composition, depending upon their particular application. They share the common characteristic of encapsulating microbubbles or micro-channels which provide for echogenic properties. Because of the different needs of various physiological chambers or sites, contrasting the vascular system with the gastrointestinal system, different sized particles will be employed with different physiologically acceptable compositions. In some applications, the particles may be coated with a physiologically acceptable coating, which will be stable under the conditions of use. The particles will generally comprise at least 10% by volume of gas, usually from about 10 to 100% by volume and may expand to greater than the volume of the particle.

Various compositions may be used for preparing the particles. Compositions which may be satisfactorily employed include physiologically acceptable amino acids, oligopeptides, and carboxyylic acids, primarily low molecular weight organic compounds under 5 kDal, usually under 2 kDal, particularly mono-tricarboxylic acids of from about 2 to 6 carbon atoms. Illustrative compounds which may find use include proline, asparagine, diglycine, phenylalanine, citric acid, α-ketoglutaric acid, galacturonic acid, sorbitol, raffinose, alloxan, oxalic acid and glutaric acid. The compositions are frequently found as hydrates, having stable waters of hydration.

The particles may be produced in a variety of ways, where the particle forming composition crystallizes from a liquid, either solution or melt, to form particles under conditions where gas is entrapped. Where crystallization from a solution is employed, the matrix forming composition is dissolved in a solvent at an elevated temperature, where the matrix forming composition is relatively insoluble at ambient or lower temperatures. Thus, the matrix forming composition is dissolved at an elevated temperature, where by allowing for evaporation and/or cooling, crystallization occurs. The supernatant may then be removed and the solvent further evaporated to insure that substantially all of the solvent has been removed. Optionally, an intermediate step may be introduced, which comprises washing the matrix forming composition at an elevated temperature with a hydrophilic solvent, which resolves in some or complete dissolution. The matrix forming material may then be harvested as described above. The drying for both stages may be achieved at mildly elevated temperatures, substantially below the melting and decomposition point of the matrix forming material. The crystals are then reduced in size to the desired size range by conventional means, e.g., mechanical grinding, milling, crushing, etc. and may be further separated as to size by sieving or other convenient means.

Citric acid microparticles can be produced by course milling raw material and then heating the particles in a moisture free environment at 50° C. tot several hours. The material can be ball milled in dry air to reduce particle size to acceptable levels, sieved, sorted, and stored in an air tight container.

Alternatively, with elevated temperature stable compounds, the matrix forming material may be heated to form a melt, where, if desired, a small amount of a second material may be used to reduce the melting point below the temperature of the pure component. With the melt, it will be desirable to use sonication to provide for cavitational formation of microbubbles in the melt. Employing power levels in the range of about 300 to 400 Watts for a short time, for about 10 to 100 sec, the desired formation of microbubbles can be achieved. Once the microbubbles are formed, the mixture may be cooled whereby gas is entrapped and then lightly crushed to diminish in size any large particles. Desirably, the crystalline product is then aged at an elevated temperature in dry air, generally in the range of about 50° to 10° C., for about 1 to 14 days, which provides for a state of complete dehydration. After the aging process, the matrix forming material may be mechanically reduced in size and the desired size range segregated by sieving.

In some instances, it will be desirable to provide for a stable protective coating of the particles. The coating may be applied by any convenient means, such as spraying, phase separation, passing the particles through the coating material, dipping, or the like. The particular amount of coating is not critical, so long as the desired thickness and uniformity of the coating is achieved, to provide the desired stability during use and dissolution, as appropriate. Various materials may be used as coatings, such as naturally occurring or synthetic polymers which can form a melt or are soluble in a nonaqueous media. The coat thickness will be in the size range of 200 Angstroms to a few microns depending upon the use application. Examples of such polymers coating compositions include ethyl cellulose, cellulose acetate, poly DL-lactide, poly DL-glycolide, polyphenylphthalamide, polyamide, polyacryldextran, polymethylmethacrylate, and polyalkylcyanoacrylate.

One group of compositions which is used to prepare the matrix will generally have a low solubility in water under ambient conditions, usually under 35 g/100 ml, preferably under about 15 g/100 ml; the other group will have a much higher water solubility, usually greater than about 150 g/ml, preferably greater than about 200 g/ml and less than about 500 g/ml, more usually less than about 350 g/ml. The particles for use in the vascular system will generally be of a size not greater than about 10 $\mu$, usually not greater than about 5 $\mu$, generally greater than about 0.5 $\mu$, more usually greater than about 1 $\mu$. The particles should be able to have a residence time of at least about 30 sec, preferably at least about 60 sec and may have residence times of 150 sec or more. By contrast, particles for the gastrointestinal tract may be substantially larger, generally greater than about 5 $\mu$, more usually greater than about 15 $\mu$ and may be 50 $\mu$ or greater. Long residence times are desirable, generally greater than about 1 h, more usually equal to or greater than about 3 h and residence times may be 8 h or greater in the gastrointestinal tract. The bubbles or microchannels, depending upon whether the gas is released, will generally range in size from about 0.5 to 10 $\mu$, more usually from about 1 to 5 $\mu$ in diameter. By appropriate selection of materials for forming the matrix, one can provide for relatively low levels of bubble coalescence, so that the small sized bubbles will be retained to provide the desired echogenic properties.

While not wishing to be held to any theory, for the sake of simplicity and technical discussion, consider a matrix particle as spherical, composed of a material soluble in blood. This particle possesses multiple tubules and channels directed inward which permits the aqueous solvent to wick in toward its center. Further, consider two different materials, one which is extremely soluble in water, such as citric acid, and another which is slightly soluble in water, such as asparagine. If the number of capillary channels is large, one can construct a model of the wicking/dissolving process. Consider two separate spiral waves moving inward toward the center. The innermost wave moves at the velocity of the capillary front, $V_c$, which depends upon the minimal crack dimension, surface tension and wetting characteristics between the solid material and the solvent. The process is somewhat more complicated and also depends upon viscous shear stress of the moving fluid and pressurization of entrapped gas.

The second wave moves with velocity $V_d$ and is pictured as the outer solid surface which moves inward as the particle dissolves. Dissolution depends upon the solubility coefficient of the particle in the aqueous liquid, the local level of saturation, convection of the outermost surface, and the particle size. If particle solubility is low in solvent, $V_c$ is greater than $V_d$, the capillary wave moves inward faster than it can dissolve, forcing the gas ahead of it and compressing the gas and increasing diffusion to the advancing liquid at the particle center. Gas remains within the particle, but the equivalent size decreases over time. Microbubbles are not released. These particles remain echogenic until the equivalent bubble size falls below the ultrasonic echo equipment.

The alternative condition occurs when $V_d$ is greater than $V_c$. In this case, the outer wall dissolves faster than the capillary wave moves inward. Therefore, there is no capillary wave. The outermost wall dissolves rapidly, constantly exposing the microtubules, channels, etc. and the liberated gas forms microbubbles almost instantly. If the process is relatively fast, formed bubbles do not linger on the surface and float away with the local flow. Both conditions can be made visible under the microscope.

Citric acid is highly soluble in water (240 g/100 ml). When matrix particles fabricated from citric acid crystals are placed in water, thousands of microbubbles are produced. These bubbles are released into a viscous fluid saturated in citric acid and remain stable for long periods of time. The free bubbles become the contrast agent. By contrast, if amino acid L-asparagine, which has a low solubility in water (3.53 g/100 ml) is placed in water, the effect observed is that of $V_c$ being greater than $V_d$. The wicking wave can be seen moving inward by the relative translucency of the particle. If both agents are employed in an in vitro flow situation, the contrast effect of each is similar.

The contrast agents of the present invention are detectable by conventional ultrasonic scanning equipment and translated into images by means of the echogenic properties of the bubbles and their different acoustical properties in relation to liquids and solids. The particles provide for a cloud of very small substantially uniform microbubbles, that when introduced into a body chamber, such as a blood vessel, the blood stream can appear opaque, as a result of the microbubbles filling the vessel. Alternatively, a lesser microbubble concentration may be provided. One can thus achieve superior contrast and contrast control.

By virtue of the ability to control the level of microbubbles formed, small effects can be observed in the blood vessel, i.e., the degree of turbulence near the walls of the vessel and the inner structure can be discerned. The small particles allow for ultrasonic contrast in capillary systems, shunts, either due to the presence or absence of microbubbles, and the like.

The subject particles may be administered as a dispersion or suspension into the blood stream by injection, catheterization, etc., and into the gastrointestinal tract by the same means or orally. The ultrasonic image is obtained from the stream opposite a location where the dispersion has dissolved or dissipated and the microbubbles are present. Blood flow rate can be determined by simultaneously measuring the positions and velocities of microbubbles or of the cloud of microbubbles. The intensities of two ultrasonic images, one from a proximal wall and the other from a distal wall of a blood vessel, can be used to measure blood flow rate. The boundary between the flowing blood and the blood vessel can be observed for evidence of turbulence which may be the result of plaques on the vessel wall.

The matrix particle will usually be administered as a dispersion in a carrier liquid. The carrier liquid is chosen to act as a dispersant, allowing for dispersing the particles without instantaneous dissolution, and to act to provide a viscous bolus for transport to the administration site and into the fluid in the chamber. The carrier liquid can also provide for stabilization of the microbubbles, and serve with the matrix material to form a microenvironment about the particles and free microbubbles.

For the most part, water will be the major constituent and additives will be present in under 25 volume %, which additives will provide desired properties of surface tension, viscosity, surfactant properties, etc. Of particular use are alkylene glycols of from 2 to 3 carbon atoms, D5W, cyclodextrins, proteins, saccharides, polyols, e.g., glycerol, xylitol, etc. in from about 5 to 20 volume %. Therefore, polyols, having at least 2 hydroxyl groups and up to and including the thousands of hydroxyl groups of cyclodextrin, find use.

The amount of liquid carrier and matrix will vary widely depending upon the chamber to be scanned, the purpose of the scan, the nature of the matrix and the like. The volume introduced may be as little as 0.1 ml and may be 10 ml or more depending on the various factors designated above, as well as the duration of the test. The concentration of matrix particles will vary widely and can be optimized during administration in accordance with the observed signal. The matrix particles may be used up to about 100 mg i.v. and 1 g or more for gastrointestinal studies.

The following examples are offered by way of illustration and not by way of limitation.

EXPERIMENTAL

Example 1. Particles from L-Asparagine and L-Proline

In 3 ml of ethanol was dispersed one gram of the subject amino acid. The suspension was placed over low heat ($\leq 50°$ C.) while constantly stirred. After all the particulates were suspended, the suspension was removed from the heat and allowed to stand under a chemical hood maintained under low humidity conditions. After 20 min, the clear liquor was poured off the top and the remainder spread into glass Pyrex plates. The material was lumpy, appearing something like flour dough. It was spread on the plate and allowed to stand under a chemical flow hood for 4 h under low humidity conditions. Most of the remaining alcohol was evaporated during this time. The nearly dry agent was placed in an oven maintained at 46° C. (While temperatures above 55° C. were used, the matrix material became somewhat discolored, although this temperature was well below its melting and decomposition points). Following drying, the material was ball-milled in dry air, sieved and stored in jars with airtight lids to prevent absorption of water, the materials being hygroscopic. The particles could be sieved to the desired size range of under 10 μ.

Example 2. Preparation Matrix Particles from Citric Acid

Citric acid crystals were placed in a Pyrex beaker and heated at 50° C. for 4 h. The material was ball milled in dry air to reduce particle size to acceptable levels, sieved, sorted, and stored in an air tight container. In the particle experiment, particle size was less than 38 microns.

Example 3. Alternative Preparation of Citric Acid Matrix Particles

Citric acid crystals were placed in a Pyrex beaker and heated to melting at 153° C. The melting was performed under a chemical flow hood to avoid exposure to fumes. The beaker was removed from the heat and placed under an Excel 202 sonicator (Heat Systems Inc.) at a power setting of 7 (340 W ultrasonic power). The rarefaction of the high intensity wave cavitates the molten liquid, which results in the formation of millions of microbubbles and the formation of foam. After about 20 sec of operation, the liquid forms stable microbubbles. The liquid is removed from the sonicator and placed in a cool, dry area. The matrix material is pried out of the beaker, lightly crushed to eliminate large chunks and the materials spread out on a Pyrex plate. It is then dried or aged in an oven at 70° C. for approximately one week. The material is then milled by mortar and pestle or ball-mill to reduce particle size to acceptable levels, sieved and stored in airtight containers. In the particular experiment, the particle size was down to about 38 $\mu$, although the desired size is 8 $\mu$ or less. The matrix particles show the irregular, lumpy, amorphous appearance common to matrix particles. A scanning electron micrographic demonstrated amorphous character.

The advantages of the sonicated citric acid method are that the material is less dense, dries Easter, and breaks up into small particles more readily.

Example 4. Particle Evaluation

Demonstration of utility of the matrix particle agents was shown in an in vitro situation using an ultrasonic scanner. A gravity flow system was developed, where degassed water flows from a reservoir to a sinuous tube approximately ½ inch in diameter and out through a discharge valve into a collection tank located below the test section. The sinuous test section was fabricated from latex with wall thicknesses of approximately 1 mm. The test section was submerged in a small container of degassed water, approximately 2 in below the surface. The contrast agent could be introduced upstream of the test section through a Y-fitting. The test section setup provided approximately 5 sec of transit time depending upon the flow of velocity. A Circadian Scan Mate II ultrasonic scanner was positioned directly above the thin walled tubing. The wavy vessel wall could not be seen by the scanner. The echogenicity of the contrast agent was necessary to make the inner wall visible.

For qualitative comparisons, established standards were used for comparison. These standards included sodium chloride and sucrose as prepared by U.S. Pat. No. 4,442,843, sonicated albumin as prepared by U.S. Pat. No. 4,718,433, gelatin foam as prepared by U.S. Pat. No. 4,276,885 and enhanced by sonication using an Excel sonicator (Heat Systems Inc.) with power setting of 6 for a few seconds and DSW with cavitation or hand shaken microbubbles. When the sonicated volume became foamy, 2 drops of glutaraldehyde were added with continuing sonication until the foam became rigid. The cross-linked gelatin was dried and broken up to form 20 micron foam particles. Test results were judged subjectively by establishing a scale from 0 to 4, where 0 represented no contrast effect and 4 represented complete and total opacification of the simulated vessel with both the top and bottom walls visible. A score of two represented approximately one-half of the maximum optimal density. Injection samples were weighed so that the same 100 mg with 2 ml of excipient was used for each test injection with the exception of the liquid delivery. The agent was flushed with 6 ml of water. Test scores are the average value of 2 readers. Table 1 represents the summarized results for a number of candidate agents and ordered by the test scores.

TABLE 1

Comparison of Echo Contrast Agents in In Vitro Model

| Description of Agent | Score | Score Ratio to Albunex | Notes |
|---|---|---|---|
| NaCl | 4 | 1.1 | Very Good Opacification |
| Citric Acid "Dried" | 4 | 1.1 | Exceptionally Good |
| L-Proline | 4 | 1.1 | Exceptionally Good |
| Galacturonic Acid | 3.7 | 1.1 | |
| Bovine Albumin Bubbles | 3.5 | 1.0 | TEST STANDARD |
| Gelatin Foam | 3.5 | 1.0 | |
| L-Asparagine | 3 | 0.9 | |
| Sucrose | 3 | 0.9 | |
| Citric Acid "Undried" | 3 | 0.9 | |
| Alloxan | 2.7 | 0.8 | |
| Sorbitol | 2.7 | 0.8 | |
| Egg Albumin Bubbles | 2.5 | 0.7 | |
| Raffinose | 1.7 | 0.5 | |
| Cavitated D5W | 1.7 | 0.5 | |
| Shaken D5W | 1.5 | 0.4 | Some very large bubbles |
| L-Arginine | 1.0 | 0.3 | |
| Water | 0 | 0.0 | |

These results indicate that citric acid and L-proline matrix particles are equal to or superior to other test agents. Asparagine does not form free bubbles, but still provides good contrast which shows that the contrast effect comes from the entrapped gas within the microchannels of the particles. All materials which yield a reading of 2.5 or greater define the lumen of the flow tube and would provide adequate contrasts.

The next study was involved with bubble life. In some applications, it is desirable to have bubbles dissolve immediately after making the measurement, while in other applications, particularly when bubbles are administered on the venous side of the arterial tree for arterial use, bubbles must be stabilized to permit passage through the lungs.

In order to assist this characteristic, a static chamber experiment was performed using the same ultrasonic scanner as described above, the same scoring system and the same injected mass. A 500 ml beaker was filled with degassed water and the scanner oriented downward. Candidate agents could be injected into the beaker and followed for an extended period of time.

The immediate reading, the half life and the time loss of signal are tabulated in the following Table 2.

TABLE 2

Potential Agent Half Life Study

| Description of Agent | Inst Reading | Half-Life sec | Total Life sec |
|---|---|---|---|
| Gelatin Foam | 3.7 | >10 min | >10 min |
| Bovine Albumin Bubbles | 3.2 | 225 | >10 min |
| Egg Albumin Bubbles | 3.5 | 100 | 270 |
| Galacturonic Acid | 3.7 | 35 | 180 |
| Citric Acid (200 mg) | 3.5 | 35 | 85 |

TABLE 2-continued

| Potential Agent Half Life Study | | | |
|---|---|---|---|
| Description of Agent | Inst Reading | Half-Life sec | Total Life sec |
| Citric Acid (100 mg) | 3 | 25 | 75 |
| L-Proline | 4 | 25 | 70 |
| L-Asparagine | 2.7 | 30 | 70 |
| NaCl | 4 | 35 | 60 |
| Alloxan | 2.7 | 25 | 50 |
| Sorbitol | 2.7 | 20 | 50 |
| Raffinose | 1.7 | 17 | 40 |

The results of Tables 1 and 2 demonstrate that the subject matrix agents are effective ultrasonic contrast agents. The agents with protective outer layers exhibit extended lifetimes, beyond the lifetimes of the subject matrix particles, where the same protective layers may be used with the matrix particles to provide an extended lifetime.

To demonstrate the formation of microbubbles, citric acid particles were screened down through a 38 μ sieve. A drop of propylene glycol was placed on top of the particles covering a plurality of them. A few bubbles formed, rose to the surface and were removed. The submerged particles were moved apart leaving only individual particles separated one from another by at least one particle diameter. Water was then added to the glycol. Within seconds, microbubbles streamed from the particles, the bubbles issuing from microcracks and around the periphery.

It is evident from the above results, that the subject matrix particles provide ultrasonic contrast media having superior properties for use in biological applications in a variety of compartments in the body. The particles show excellent echogenicity, can be readily prepared, and safely administered to a mammalian host. Thus, the subject invention provides new materials for ultrasonic contrast which have properties equal to or superior to commercially available products.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a method for ultrasonic scanning comprising introducing an echogenic material into a liquid containing chamber; isonating said chamber with ultrasonic sound; and detecting echoes from said chamber as a result of said echogenic material to determine characteristics of the walls of said chamber or of the fluid in said chamber, the improvement which comprises:

said echogenic material being individual matrix particles, characterized by being comprised of low molecular weight physiologically acceptable amino acids capable of forming microparticles with entrapment of gas as microtubules, microchambers, and/or microcracks; and either capable of rapid dissolution in said liquid with release of microbubbles which retain a size to be visualized by standard ultrasonic techniques; or by slow dissolution in said liquid.

2. A method according to claim 1, wherein said matrix particles are anhydrous and said amino acids exist as hydrates.

3. A method according to claim 1, wherein said amino acids are asparagine or proline.

4. A method according to claim 1, wherein said matrix particles are produced by dissolving said amino acids in a solvent at an elevated temperature; precipitating said amino acids from said solvent by at least one of evaporation or cooling; and removing residual solvent.

5. A method according to claim 7, wherein said amino acids are proline or asparagine.

6. A method according to claim 1, wherein said matrix particles are produced by melting said amino acids by heating said amino acids above their melting point; and cooling said amino acids while sonicating said amino acids to produce microtubules of entrapped gas.

* * * * *